(12) United States Patent
Hedevarn (10) Patent No.: US 12,320,348 B2
(45) Date of Patent: *Jun. 3, 2025

(54) PERISTALTIC PUMP (71) Applicant: OINA VV AB, Nacka (SE)

(72) Inventor: Torbjorn Hedevarn, Vasteras (SE)

(73) Assignee: OINA VV AB, Nacka (SE)

(*) Notice: Subject to any disclaimer, the term of this patent is extended or adjusted under 35 U.S.C. 154(b) by 0 days.

This patent is subject to a terminal disclaimer.

(21) Appl. No.: 18/327,575

(22) Filed: Jun. 1, 2023

(65) Prior Publication Data

US 2023/0304489 A1 Sep. 28, 2023

Related U.S. Application Data (63) Continuation of application No. 16/762,293, filed as application No. PCT/SE2018/051101 on Oct. 29, 2018, now Pat. No. 11,692,540.

(30) Foreign Application Priority Data

Nov. 8, 2017 (EP) .................................... 17200613

(51) Int. Cl.
*F04B 43/12* (2006.01)
*A61M 60/279* (2021.01)

(52) U.S. Cl.
CPC ....... *F04B 43/1284* (2013.01); *A61M 60/279* (2021.01); *F04B 43/1261* (2013.01)

(58) Field of Classification Search
CPC .. F04B 43/0009; F04B 43/12; F04B 43/1253; F04B 43/1261; F04B 43/1284; F04B 53/22; A61M 60/279

(Continued)

(56) References Cited

U.S. PATENT DOCUMENTS 2,434,802 A 1/1948 Jacobs
2,913,992 A 11/1959 Blue et al.
(Continued)

FOREIGN PATENT DOCUMENTS

CA 172028 S 8/2017
CA 177819 S 11/2018
(Continued)

OTHER PUBLICATIONS

Extended European Search Report for Application No. 17200613.2 dated Apr. 30, 2018 (7 pages).
(Continued)

*Primary Examiner* — Kenneth J Hansen
*Assistant Examiner* — Chirag Jariwala
(74) *Attorney, Agent, or Firm* — Edell, Shapiro & Finnan, LLC (57) ABSTRACT A peristaltic pump includes a motor, a rotor coupled to the motor, a housing in which the rotor is arranged, and an opening and closing mechanism. The mechanism includes a tube pressuring portion, a slider, and a pivotable cover coupled to the housing and the slider and the mechanism is connected to the slider and the tube pressuring portion such that a tube engaging surface of the tube pressuring portion slides towards and away from the rotor upon closing and opening of the pivotable cover. The opening and closing mechanism further includes a slider moving element attached to the slider, the pivotable cover including a rotating shaft having an extension configured to engage the slider moving element for moving the slider and also the tube pressuring portion away and towards a top of the housing in response to a respective opening and closing of the pivotable cover.

20 Claims, 6 Drawing Sheets (58) Field of Classification Search
USPC .................................................... 417/477.1
See application file for complete search history.

(56) References Cited

U.S. PATENT DOCUMENTS

| | | | |
|---|---|---|---|
| 3,289,232 A | 12/1966 | Beach | |
| 3,353,491 A | 11/1967 | Bastian | |
| 3,675,653 A | 7/1972 | Crowley et al. | |
| 3,740,173 A | 6/1973 | Natelson | |
| 3,963,023 A | 6/1976 | Hankinson | |
| 3,990,444 A | 11/1976 | Vial | |
| 4,025,241 A | 5/1977 | Clemens | |
| 4,155,362 A | 5/1979 | Jess | |
| 4,189,286 A | 2/1980 | Murry et al. | |
| 4,193,398 A | 3/1980 | Refson | |
| 4,233,001 A | 11/1980 | Schmid | |
| 4,256,442 A | 3/1981 | Lamadrid | |
| 4,544,336 A | 10/1985 | Faeser et al. | |
| 4,552,516 A | 11/1985 | Stanley | |
| 4,558,996 A * | 12/1985 | Becker | F04B 43/1253 417/374 |
| 4,673,334 A | 6/1987 | Allington et al. | |
| 4,708,604 A | 11/1987 | Kidera | |
| 5,083,908 A | 1/1992 | Gagnebin et al. | |
| 5,096,393 A | 3/1992 | Van Steenderen et al. | |
| 5,110,270 A | 5/1992 | Merrick | |
| 5,380,173 A | 1/1995 | Hellstrom | |
| 5,388,972 A | 2/1995 | Calhoun et al. | |
| 5,401,328 A * | 3/1995 | Schmitz | B08B 3/02 134/200 |
| 5,403,277 A | 4/1995 | Dodge et al. | |
| 5,447,417 A | 9/1995 | Kuhl et al. | |
| 5,626,563 A | 5/1997 | Dodge et al. | |
| 5,628,731 A | 5/1997 | Dodge et al. | |
| 5,709,539 A | 1/1998 | Hammer et al. | |
| 5,904,668 A | 5/1999 | Hyman et al. | |
| 5,928,177 A | 7/1999 | Brugger et al. | |
| 5,993,420 A | 11/1999 | Hyman et al. | |
| 6,019,582 A | 2/2000 | Green | |
| 6,186,752 B1 | 2/2001 | Deniega et al. | |
| 6,419,466 B1 | 7/2002 | Lowe et al. | |
| 6,494,692 B1 | 12/2002 | Green | |
| 6,494,693 B1 | 12/2002 | Sunden | |
| 7,287,968 B2 | 10/2007 | Haser et al. | |
| 7,434,312 B2 | 10/2008 | Christenson et al. | |
| 7,462,022 B2 | 12/2008 | Fromm | |
| 7,478,999 B2 | 1/2009 | Limoges | |
| 7,722,338 B2 | 5/2010 | Nordell et al. | |
| 8,052,399 B2 | 11/2011 | Stemple et al. | |
| 8,083,503 B2 | 12/2011 | Voltenburg, Jr. et al. | |
| 8,128,384 B2 | 3/2012 | Mou | |
| 8,152,498 B2 | 4/2012 | Bunoz | |
| 8,297,955 B2 | 10/2012 | Fujii | |
| 8,403,656 B2 | 3/2013 | Fromm | |
| 8,550,310 B2 | 10/2013 | Alstad et al. | |
| D700,915 S | 3/2014 | Damhuis et al. | |
| 8,757,991 B2 | 6/2014 | Maitre et al. | |
| D709,611 S | 8/2014 | Burger et al. | |
| D710,901 S | 8/2014 | Brokenshire et al. | |
| 8,840,382 B1 | 9/2014 | Al-Harbi | |
| 8,905,730 B2 | 12/2014 | Ashburn | |
| 8,985,981 B2 | 3/2015 | Fromm et al. | |
| D730,408 S | 5/2015 | Brokenshire et al. | |
| D734,366 S | 7/2015 | Hoglund et al. | |
| D735,241 S | 7/2015 | Brokenshire et al. | |
| 9,072,540 B2 | 7/2015 | Jarnagin et al. | |
| 9,239,049 B2 | 1/2016 | Jarnagin et al. | |
| D765,522 S | 9/2016 | Spraw et al. | |
| D766,988 S | 9/2016 | Crowley et al. | |
| D766,989 S | 9/2016 | Crowley et al. | |
| D766,990 S | 9/2016 | Crowley et al. | |
| D767,118 S | 9/2016 | Hyde et al. | |
| 9,518,576 B1 | 12/2016 | Wiederin et al. | |
| 9,562,528 B2 | 2/2017 | Warren | |
| D788,178 S | 5/2017 | Theiss | |
| 9,657,731 B2 | 5/2017 | Miyazaki et al. | |
| 9,810,210 B2 | 11/2017 | Bassani | |
| 9,822,775 B2 | 11/2017 | Crowsley | |
| 9,863,413 B1 | 1/2018 | Wiederin et al. | |
| 9,925,315 B2 | 3/2018 | Eubanks et al. | |
| D826,281 S | 8/2018 | Mead et al. | |
| 10,060,425 B2 | 8/2018 | Schnekenburger et al. | |
| 2002/0019612 A1 | 2/2002 | Wantanabe et al. | |
| 2005/0069436 A1 | 3/2005 | Shibasaki | |
| 2005/0254978 A1 | 3/2005 | Shibasaki | |
| 2005/0196307 A1* | 9/2005 | Limoges | F04B 43/1253 417/474 |
| 2007/0140880 A1 | 6/2007 | Fulmer | |
| 2007/0217932 A1 | 9/2007 | Voyeux et al. | |
| 2007/0224063 A1 | 9/2007 | Postma et al. | |
| 2007/0258838 A1 | 11/2007 | Drake et al. | |
| 2008/0175734 A1 | 7/2008 | LaBanco et al. | |
| 2008/0213113 A1* | 9/2008 | Lawrence | F16L 3/1041 417/477.2 |
| 2009/0129944 A1 | 5/2009 | Stemple | |
| 2010/0224547 A1 | 9/2010 | Fujii | |
| 2011/0004161 A1 | 1/2011 | Ito | |
| 2011/0165005 A1* | 7/2011 | Maitre et al. | F04B 43/1276 418/45 |
| 2011/0300010 A1 | 12/2011 | Jarnagin et al. | |
| 2013/0052063 A1 | 2/2013 | Schoenewerk | |
| 2013/0115120 A1 | 5/2013 | Jarnagin | |
| 2014/0294633 A1 | 10/2014 | Brokenshire | |
| 2014/0301878 A1 | 10/2014 | Will et al. | |
| 2015/0159643 A1 | 6/2015 | Koob | |
| 2015/0204321 A1* | 7/2015 | Schnekenburger | F04B 53/16 417/477.2 |
| 2016/0017880 A1 | 1/2016 | Maguire | |
| 2016/0312774 A1 | 10/2016 | Oude Vrielink | |
| 2018/0003169 A1 | 1/2018 | Van Stell | |
| 2018/0245579 A1 | 8/2018 | Mead et al. | |
| 2018/0266410 A1 | 9/2018 | Oude Vrielink | |
| 2018/0274538 A1 | 9/2018 | Staedele et al. | |
| 2018/0298897 A1 | 10/2018 | Staedele et al. | |
| 2018/0306183 A1 | 10/2018 | Staedele et al. | |

FOREIGN PATENT DOCUMENTS

| | | |
|---|---|---|
| CN | 201155446 Y | 11/2008 |
| CN | 101336343 A | 12/2008 |
| CN | 101918714 A | 12/2010 |
| CN | 101959548 A | 1/2011 |
| CN | 301867507 | 3/2012 |
| CN | 103874857 A | 6/2014 |
| CN | 303143850 | 3/2015 |
| CN | 303454194 | 11/2015 |
| CN | 303591279 | 2/2016 |
| CN | 303949618 | 11/2016 |
| CN | 206495770 U | 9/2017 |
| CN | 304438151 | 1/2018 |
| CN | 304926938 | 12/2018 |
| EM | 002446179-0001 | 4/2014 |
| EM | 002446179-0002 | 4/2014 |
| EP | 0013002 A1 | 7/1980 |
| EP | 0248653 A2 | 12/1987 |
| EP | 0473348 A1 | 3/1992 |
| EP | 0547726 A1 | 6/1993 |
| EP | 2253345 A1 | 11/2010 |
| EP | 121077 B1 | 9/2011 |
| EP | 2098729 B1 | 5/2012 |
| EP | 2380614 B1 | 11/2012 |
| EP | 2380615 B1 | 11/2012 |
| EP | 2232074 B1 | 8/2018 |
| EP | 2116725 B1 | 9/2018 |
| EP | 3483440 A1 | 5/2019 |
| FR | 8654088 A | 4/1940 |
| GB | 1196374 A | 6/1970 |
| GB | 2051253 B | 11/1983 |
| GB | 2570320 A | 7/2019 |
| GB | 2570713 A | 8/2019 |
| IN | 102076370 A | 5/2011 |
| JP | 5627151 B2 | 11/2014 |
| WO | 2006008376 A1 | 1/2006 |

(56)  References Cited

FOREIGN PATENT DOCUMENTS

| | | |
|---|---|---|
| WO | 2006110510 A2 | 10/2006 |
| WO | 2007038364 A2 | 4/2007 |
| WO | 2010000702 A1 | 1/2010 |
| WO | 2012009697 A1 | 1/2012 |
| WO | 2013165094 A1 | 11/2013 |
| WO | 2018101113 A1 | 6/2018 |

OTHER PUBLICATIONS

International Search Report and Written Opinion for Application No. PCT/SE2018/051101 dated Jan. 21, 2019 (10 pages).
Office Action for Chinese Patent Application No. 201880072303.0 dated Sep. 3, 2021 with English translation, 3 pages.

* cited by examiner

PERISTALTIC PUMP

CROSS REFERENCE TO RELATED APPLICATIONS

This application is a continuation of U.S. patent application Ser. No. 16/762,293, filed May 7, 2020, entitled "Peristaltic Pump," which was a national stage application of International Application No. PCT/SE2018/051101, filed Oct. 29, 2018, which claims priority to European Patent Application No. 17200613.2, filed Nov. 8, 2017. The entire disclosure of each of the foregoing applications is incorporated herein by reference.

TECHNICAL FIELD

The invention relates to the field of peristaltic pumps for various applications. One application field is the medical field. The peristaltic pump according to the invention comprises some unique features in particular an opening and closing mechanism that is accentuated by a pivotable cover, which pivotable cover is connected to a tube pressuring portion via elastic elements. The elastic elements are thereby connected via at least one adjustable element so that the tension or pre-tension in the elastic element can be adjusted to tube types and material, to the viscosity of the pumped fluid and to the amount of fluid that needs to be pumped.

BACKGROUND OF THE INVENTION

In the medical field peristaltic pumps are used quite often, since this technology allows to avoid contact between the fluid (gas or liquid) to be pumped and the actual pump via a tube. Peristaltic pumps for medical applications are usually integrated in units that comprise other devices, for instance in intensive care units. The peristaltic pumps are typically used for a comparably long time and since they help to keep up vital functions a failure of a peristaltic pump is not an option. Peristaltic pumps used in medical applications have to be reliable and durable.

Many prior art pumps comprise mechanism that press a tube comprising a fluid to be pumped towards a rotor having rollers or the like so that the rollers can push the fluid in the tube. Such mechanism further comprise holders or clamps that squeeze the tube on inlet- and outlet side of the pump so that the rotor, which is arranged in between the holder on the inlet side and the holder on the outlet side, cannot move the tube when rotating and thus pumping the fluid. The clamping or holding on the inlet side is thereby more important than the clamping or holding on the outlet side, since the rotor is urging the tube to glide in the direction of pumping and the rotor will thus draw the tube away from the inlet side of the peristaltic pump in the direction of pumping. The outlet side holder merely has the task of holding the tube in position. In known pumps such mechanisms are normally not adjustable by the operator or medical personnel. They only provide a factory set tension or pressure force for pressuring the tube towards the rotor and for holding the tube in position on the inlet and outlet side of the pump respectively. This can pose problems if the viscosity of the fluid changes or if the stiffness of the tube varies, thus if another tube material, size or strength (wall thickness) of the tube is used or if different fluid volumes need to be pumped. As medicine, oxygen, blood or other fluids can be pumped with peristaltic pumps, these pumps further have to be very precise. Therefore the construction of such peristaltic pumps has to be exact and it shall be performed with minimal tolerances.

SUMMARY OF THE INVENTION

An object of the present invention is to provide a peristaltic pump that is flexible in its use and reliable.

Another object is to provide a peristaltic pump that is durable and can be used for various applications.

A further object is to provide a peristaltic pump that is easy to use and precise.

The inventor(s) of the present invention have realized that it is possible to provide a peristaltic pump for medical applications comprising an opening and closing mechanism that is coupled to a pivotable cover, said opening and closing mechanism being adjustable in various ways so that the contact pressure of the tube towards a rotor of the peristaltic pump can be adjusted and that a clamping force of the tube, at least on a pump inlet side, can be adjusted. The opening and closing mechanism is coupled to the pivotable cover so that it is engaged and disengaged when the pivotable cover is closed and opened, respectively. The inventor(s) further realized that if the opening and closing mechanism is provided with high precision, the adjustability and accuracy further improves.

Disclosed herein is a peristaltic pump for medical applications comprising a motor, a rotor coupled to the motor, a housing in which the rotor is arranged, an opening and closing mechanism comprising a tube pressuring portion, a slider and a pivotable cover coupled to the housing and the slider. The opening and closing mechanism further comprises an elastic element connected to the slider and the tube pressuring portion so that a tube engaging surface of the tube pressuring portion slides towards and away from the rotor upon closing and opening of the pivotable cover, respectively. The housing comprises a first adjustable motion link, the tube pressuring portion comprises a frame that extends into the housing said frame comprising at least two guiding elements and in that the tube pressuring portion's movement towards and away from the rotor is guided by the at least two guiding elements, which interact with the first adjustable motion link. The tube pressuring portion comprises an adjustment element to which the elastic element is connected so that a tension in the elastic element is adjustable. The opening and closing mechanism further comprises a post attached to the slider, the pivotable cover comprising a rotating shaft having an extension extending perpendicular to a longitudinal direction defined by the rotating shaft. The extension being configured to engage the post for moving the slider and via the elastic element also the tube pressuring portion away and towards a top of the housing, when the pivotable cover is opened and closed, respectively.\

The above peristaltic pump provides an adjustable opening and closing mechanism, in which the pressure or force at which the tube pressuring portion is pressed towards the rotor can be varied and adjusted.

The post may be chamfered at its free end. Such a chamfered free end may provide an initial resistance to the actual opening movement of the pivotable cover. As soon as the extension or the free end of the extension is moved below the chamfered free end then the force needed to open the pivotable cover decreases. The chamfered free end of the post provides for a self-locking of the pivotable cover when the cover is closed and for example under adjustment. Thus even when the elastic elements are highly pre-tensioned the pivotable cover will not open due to the self-locking effect of the chamfered post. In other words, the higher the force of the pre-tensioning the more the pivotable cover wants to stay in its position.

The above explained chamfered free end of the post may be beneficial if the extension comprises a roller at its free end.

The guiding elements may be rollers, sleeve bearings, gliding surfaces or any other suitable element that can engage the first adjustable motion link. In a similar way the first and second motion links may be cam surfaces, surfaces or any other suitable motion guiding means.

The, preferably single, adjustment element is configured to adjust the pump to various system pressures. This allows to make sure that the pump is always running in its optimal range depending on the system pressure.

In an embodiment the peristaltic pump comprises a second motion link and the first adjustable motion link may be adjustable by at least one screw and the frame may comprise four guiding elements whereby two of the four guiding elements engage the first motion link and other two of the four guiding elements engage the second motion link.

The effect of the above is that the tube pressuring portion comprising the frame is guided via the first and second motion link in a kinematically overdetermined way. Thus the frame and therewith the tube pressuring portion cannot move sideways with respect to the longitudinal direction of the first and second motion link and the movement of the frame and the tube pressuring portion is very precisely and smoothly guided.

In an embodiment the peristaltic pump may comprise a bridge connecting the adjustment element to the elastic element, wherein the frame comprises a cut-out having a bottom wall and two side walls and stop protrusions extending from the two side walls. The bridge being movably arranged in the cut-out between the bottom wall and the stop protrusions.

The bottom wall is arranged at an end of the frame closest to the bottom of the peristaltic pump. The bottom wall may further comprise a through passage or the like so the adjustment element can engage the bridge. The stop protrusion prevents the bridge from being drawn too far away from the bottom wall by the elastic element in case the adjustment element is disengaged from the bridge by mistake.

In one embodiment a pair of elastic elements symmetrically parallel-connected to the adjustment element via the bridge are provided.

Two elastic elements symmetrically connected to the bridge provide for a symmetric force or tension on the bridge and thus on the tube pressuring portion.

In another embodiment the housing may comprise a front portion and a back portion and whereby the rotor is arranged in the front portion and the slider, the elastic element(s), the frame, the adjustment element and the first adjustable motion link is arranged in the back portion.

Such a separation may protect the mechanical pieces of the opening and closing mechanism in the back portion from dust and abrasion from the tube.

In another embodiment the slider may comprise a pin extending in a same direction from the slider as the post, said pin being arranged in line with the post as seen in a direction perpendicular to the longitudinal direction defined by the rotating shaft. The extension may comprise a roller that engages the post upon closing of the pivotable cover for moving the slider towards the top of the housing and the roller may engage the pin upon opening of the pivotable cover for moving the slider away from the top of the housing.

The above explained pin and post combination arranged and fixed to the slider provides for a very smooth transition and movement of the opening and closing mechanism when the pivotable cover is opened and closed, respectively. In another embodiment the peristaltic pump may comprise an adjustable adapter, whereby the elastic element(s) are connected to the slider via the adjustable adapter. The adjustable adapter may comprise a threaded shaft having a hole and a nut for fastening the latter to the slider.

This allows to change the range of pre-tension that is possible to provide with the elastic element(s) depending on application field and circumstances, such as temperature, size of tube, material of tube etc.

In a further embodiment the housing may comprise a pump inlet side and a pump outlet side, each of the pump inlet side and the pump outlet side comprising a tube receiving opening. The opening and closing mechanism may further comprise an inlet tube holder portion and an outlet tube holder portion, the inlet tube holder portion and the outlet tube holder portion being arranged next to the pump inlet side and the pump outlet side, respectively. Each of the inlet tube holder portion and the outlet tube holder portion may be configured to increase and decrease a size of the corresponding tube receiving opening upon opening and closing of the pivotable cover.

The increasing and decreasing of the size of the corresponding tube receiving opening leads to a clamping and thus a temporary fixation of the tube when the pivotable cover is closed and to a release of the tube when the pivotable cover is opened.

In a further embodiment, an elastic element connecting the inlet tube holder portion to the slider may be connected to the inlet tube holder portion via a positioning element in order to adjust a position of the inlet tube holder portion.

This allows to set the position of the inlet tube holder portion and, if wanted, to already provide a slight pre-tension in the elastic element. The above feature provides for a simple adjustment of the position of the inlet tube holder portion to various tube sizes for example.

In a further embodiment the tube pressuring portion may comprise a stop element that is configured to engage the adjustment element so that the adjustment element cannot move any longer once the tension in the elastic element(s) is set.

This may increase the reliability of the peristaltic pump and increase long-term stability of the chosen tension in the elastic element(s) used to press the tube pressuring portion towards the rotor when the pivotable cover is closed.

In another embodiment the inlet tube holder portion may comprise a pre-tension device configured to be screwed onto the adjustment element in order to provide a pre-tension in the elastic element connecting the inlet tube holder portion to the slider.

Thus the force with which the inlet tube holder portion clamps the tube when the pivotable cover is closed may be directly adjustable. In many or almost all cases at least a small engagement of the elastic element is wanted when the tube is positioned and clamped by the inlet tube holder portion. Such an adjustment may be beneficial in order to adapt the force at which the tube is clamped to tube size, the material stiffness of the tube, in some lengths also the viscosity of the fluid and the fluid pressure in the system.

In a further embodiment the inlet tube holder portion may comprise a stop element configured to engage the positioning element in order to lock the positioning element after a tension in the elastic element connecting the inlet tube holder portion to the slider has been set.

The above may increase reliability and long-term stability of the force or clamping force applied on the pump inlet side to the tube, when the tube is engaged in the pump.

The elastic elements may be springs and the adjustment elements may be screws.

The effect of using screws is that the pre-tension in the elastic elements can be steplessly adjusted.

The elastic elements or springs may even be configured to be exchangeable or interchangeable so that springs or elastic elements with various spring constants can be used and installed in the peristaltic pump.

The guiding elements are rollers and they may have a U- or V-shaped profile or any combination thereof and the first adjustable motion link is a bar configured to fit into said U- or V-shaped profile of said rollers.

The U- or V-shaped profile and the fitting of the first and second motion link respectively into said U- or V-shaped profile provides for a determined and gap-free movement. Further due to the U- or V-shaped profile (or combination thereof) the movement of the tube pressuring portion is locked in a z-direction (height) of the peristaltic pump and the noise level during movement is reduced while at the same time the accuracy is very high.

In another embodiment the rotating shaft may comprise a sensor element and the housing may comprise a corresponding sensor, the sensor element and sensor may be arranged so that it can be detected, whether the pivotable cover is open or closed.

The sensor and sensor element may be used to detect whether or not it is safe to switch on the peristaltic pump and/or to simply detect whether or not the pivotable cover is closed or open.

BRIEF DESCRIPTION OF THE DRAWINGS

The present invention will now be described, for exemplary purposes, in more detail by way of an embodiment(s) and with reference to the enclosed drawings, in which.

FIG. 5b schematically illustrates a top down view onto the part of the peristaltic pump shown in FIG. 5a;

DETAILED DESCRIPTION

Figures 1, 2:
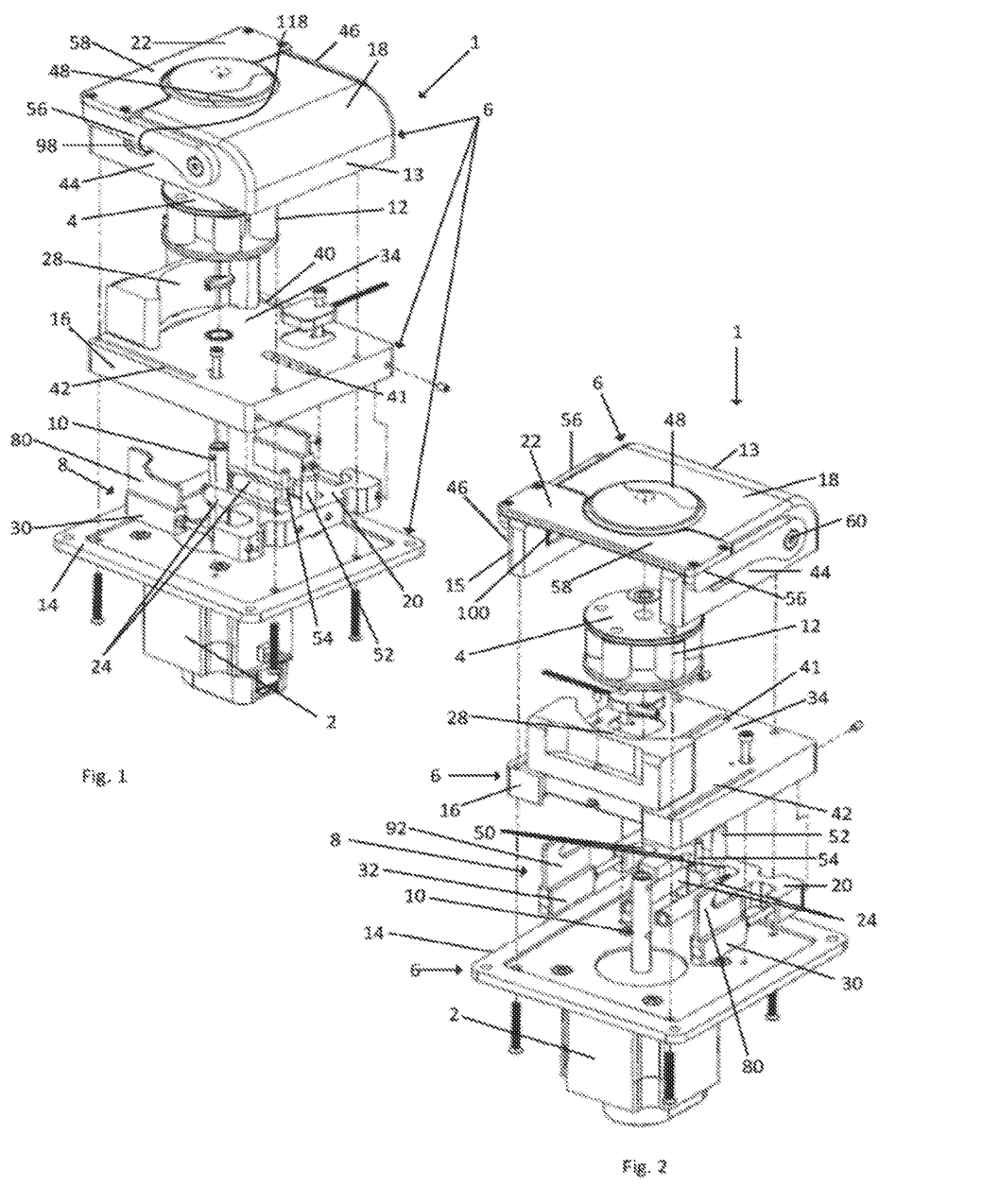
FIG. 1 schematically illustrates an exploded, perspective view of the peristaltic pump according to the invention.
FIG. 2 schematically illustrates another exploded, perspective view of the peristaltic pump according to the invention.

FIGS. 1 and 2 illustrate exploded and perspective views of a peristaltic pump 1 according to the invention. The peristaltic pump 1 comprises a motor 2, a rotor 4 and a housing 6. The motor 2 comprises a drive axis 10 that extends partially through the housing and that is connected to the rotor 4. The rotor 4 comprises drive elements 12, in the form of rollers that are configured to engage a tube (not shown) comprising a fluid to be pumped. The drive elements 12 of the rotor are arranged symmetrically along the circumference of the rotor 4. In the embodiment shown the rotor 4 comprises four drive elements 12 covering a 90° degree angle. It is however clear that any number of drive elements 12 from three (covering a 120° degree angle) upwards can be installed in the rotor.

The housing 6 comprises a base plate 14, a back portion 16 and front portion 18. The motor 2 is connected to the base plate 14 via screws and the back portion 16 and the front portion 18 are connected to the base plate 14 via screws. The housing 6 further comprises a top 13 and a bottom 15.

The back portion 16 comprises a separating wall 34 for separating mechanical parts from dust and tube residuals, an outlet side guide track 40 and an inlet side guide track 42. These guide tracks 40, 42 are configured to let a tube engaging protrusion 80, 92 of a tube inlet holder portion 30 and tube outlet holder portion 32, respectively, pass. The separating wall 34 comprises various through holes for the screws that hold the base plate 14, the back portion 16 and the front portion 18 together and for the drive axis 10 to pass through and reach the rotor 4. The through holes may further comprise O-rings in order to hermetically separate the front portion 18 from the back portion 16 of the peristaltic pump 1.

The front portion 18 comprises a pump inlet side 44 and a pump outlet side 46. The tube (not shown) that comprises the fluid (gas or liquid) to be pumped runs into the peristaltic pump 1 via the pump inlet side 44 and a tube receiving opening 98, respectively, into the area of the rotor 4, where it is held in position via a tube pressurizing portion 28 and out of the peristaltic pump 1 through the pump outlet side 46 and a further tube receiving opening 100, respectively.

The front portion 18 further comprises a window 48 made of an at least partially see-through material that allows to see from the outside of the peristaltic pump 1, if the rotor 4 is running even when a pivotable cover 22 is closed, as illustrated in FIGS. 1 and 2.

The pivotable cover 22 is part of an opening and closing mechanism 8, which will now be at least partially explained referring to FIGS. 1 and 2. The opening and closing mechanism 8 comprises a slider 20, which is embedded in the back portion 16 of the housing 6, the pivotable cover 22, two elastic elements 24 in the form of springs (can also be rubber elements or the like) and the tube pressuring portion 28. The two elastic elements 24 are coupled, via one of their ends to the slider 20 via screws comprising a receiving opening for a hook of the elastic elements 24. The elastic elements 24 are also connected to the tube pressuring portion 28. Details of this connection will be explained referring to FIGS. 5a and 5b.

The pivotable cover 22 comprises a front cover 58, which is made of an at least partially transparent material, which allows to see a tube, when it is arranged in the peristaltic pump 1. The front cover 58 is connected to a rotating shaft 60 that extends through the front portion 16, via arms 56 on the inlet side 44 and the outlet side 46, respectively.

The slider 20 comprises recesses 50, a post 52, which is chamfered at its free end and a pin 54. The slider 20 is arranged movable in the back portion 16 and the post 52 and the pin 54 are configured to extend through a longitudinal opening 41 in the separating wall 34 into the front portion 18. The post 52 and the pin 54 are configured to be engaged by the rotating shaft 60 of the pivotable cover 22 upon opening and closing of the pivotable cover.

Figure 3:
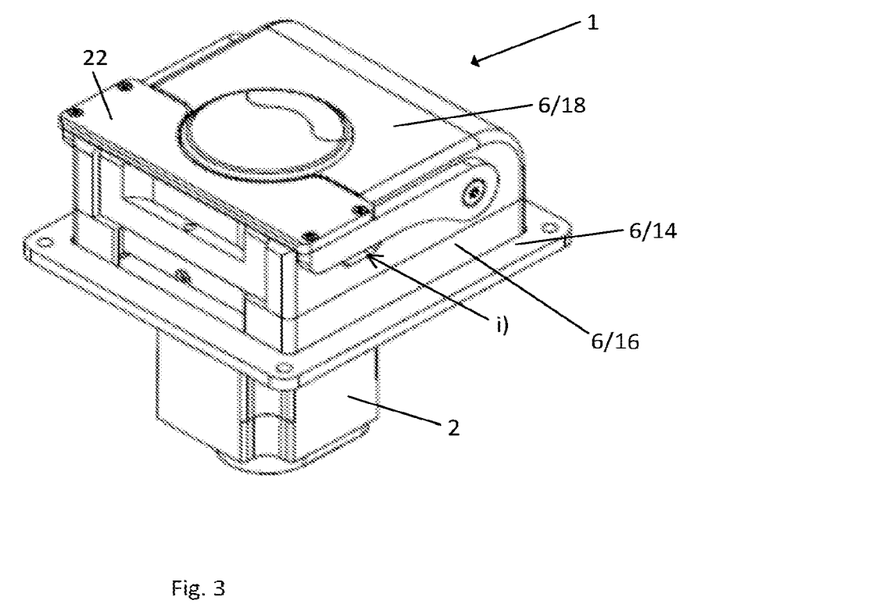
FIG. 3 schematically illustrates a perspective view of the peristaltic pump according to the invention with a pivotable cover in a closed position.

FIG. 3 illustrates a perspective view of the peristaltic pump 1 assembled and ready to be used or built into a medical unit. The housing 6 is illustrated comprising the base plate 14, the back portion 16 and the front portion 18. Further also the motor 2 is visible. The pivotable cover 22 is illustrated in the closed position. The arrow i) illustrates where a tube comprising a fluid to be pumped would enter the peristaltic pump 1.

The functioning of the opening and closing mechanism 8 will now be explained in detail referring to FIGS. 4 to 8.

Figure 4:
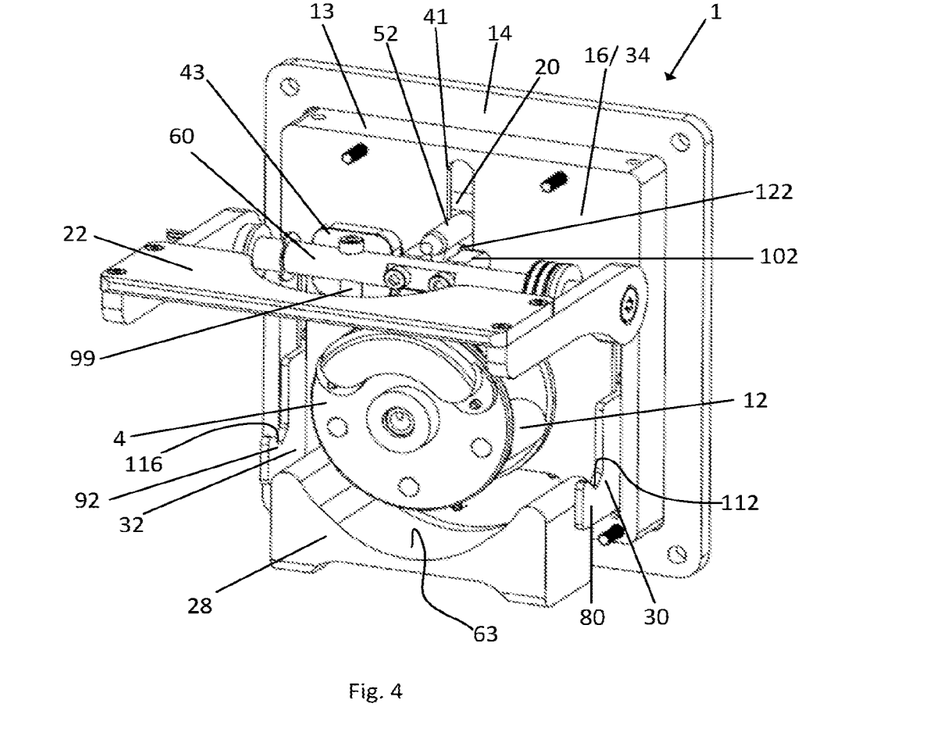
FIG. 4 schematically illustrates the peristaltic pump according to the invention with certain parts of the housing removed for illustrative purposes.

FIG. 4 illustrates the peristaltic pump 1 with the pivotable cover 22 in its open position. The front portion 18 (not shown in FIG. 4) is removed for illustrative purposes and only the back portion 16 and the base plate 14 of the housing 6 are shown. The pivotable cover 22 is in the open position and the tube pressurizing portion 28 is therewith in a position moved away from the rotor 4 so that a tube (not shown) can be placed in between a tube engaging surface 63 of the tube pressuring portion 28 and the rotor 4 and its drive elements 12, respectively. The rotating shaft 60 of the pivotable cover 22 comprises a first extension 102 or protrusion comprising a roller 122, which roller 122 engages the post 52 with the chamfered free end upon moving of the pivotable cover 22 into a closed position. The extension 102 extends in a direction more or less perpendicular to a longitudinal direction of the rotating shaft 60. By closing the pivotable cover 22 the extension 102 and the roller 122 will push the post 52 and therewith the slider 20 towards the top 13 of the housing 6 and the back portion 16, respectively. The post 52 extends through the longitudinal opening 41 in the separating wall of the back portion 16.

Still referring to FIG. 4, the rotating shaft 60 comprises a second extension 99 comprising a sensor element (not visible in FIG. 4) at its free end, which sensor element is configured to interact with a sensor 43 on the separating wall 34 of the back portion 16 of the housing 6. As can be seen in FIG. 4, the second extension 99 is also extending more or less in a direction perpendicular to the longitudinal direction of the rotating shaft 60 but about or approximately 90° offset the first extension 122. The sensor element 101 will be in comparably close contact or even in physical contact with the sensor 43 when the pivotable cover 22 is in a closed position. Thus sensor 43 is able to detect whether or not the pivotable cover 22 is in its closed position.

The sensor 43 may be a magnetic sensor such as a hall type sensor or an electromechanical sensor.

In FIG. 4, there are further the inlet tube holder portion 30 and the outlet tube holder portion 32 illustrated. Since the inlet- and outlet tube holder portions 30, 32 are also coupled, via elastic elements (not visible in FIG. 4) to the slider 20, they are also shown in a position moved away from the top 13 of the peristaltic pump 1. More specifically the inlet- and outlet tube holder portions 30, 32 are configured to change the size of the tube receiving opening 98, 100 in the front portion (c.f. FIGS. 1 and 2) and the pump inlet side 44 and the pump outlet side 46, respectively. Thus upon closing of the pivotable cover 22, the inlet- and outlet tube holder portions 30, 32 are configured to move upwards towards the top 13 of the peristaltic pump 1 in order to decrease the size of the corresponding tube receiving opening 98, 100 in order to clamp the tube (not shown) via a corresponding tube engaging protrusion 80, 92 having a V-shape 112, 116 and to increase the size of the corresponding tube receiving opening 98, 100 in order to release the tube (not shown) upon opening of the pivotable cover 22. The V-shape 112, 116 of the tube engaging protrusions 80, 92 may alternatively be U-shaped or any other shape that is able to engage a tube.

Although the outlet and inlet side are illustrated in the figures, it is clear that they can be interchanged, since the peristaltic pump is configured to fluid in both directions, which can be easily achieved by changing the direction of rotation of the rotor.

Figure 5A:
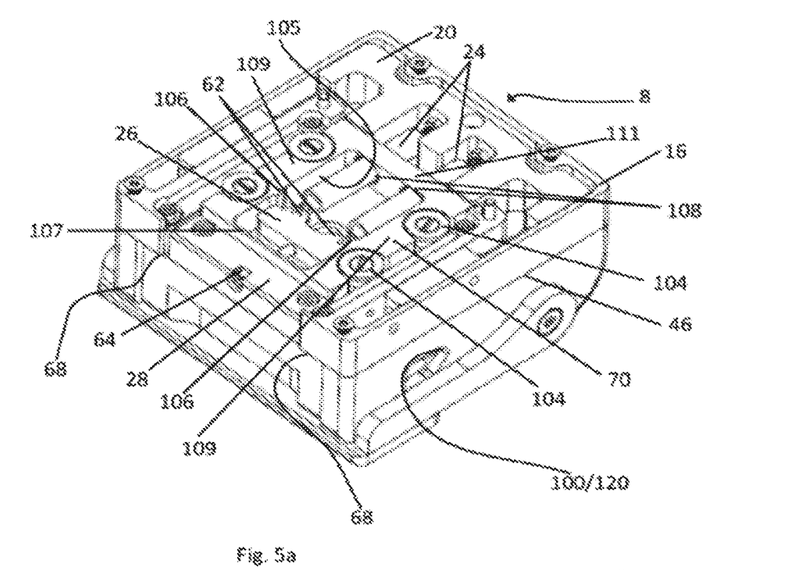
FIG. 5a schematically illustrates a perspective view of a part of the peristaltic pump according to the invention and of an opening and closing mechanism of the peristaltic pump according to the invention.
Figure 5B:
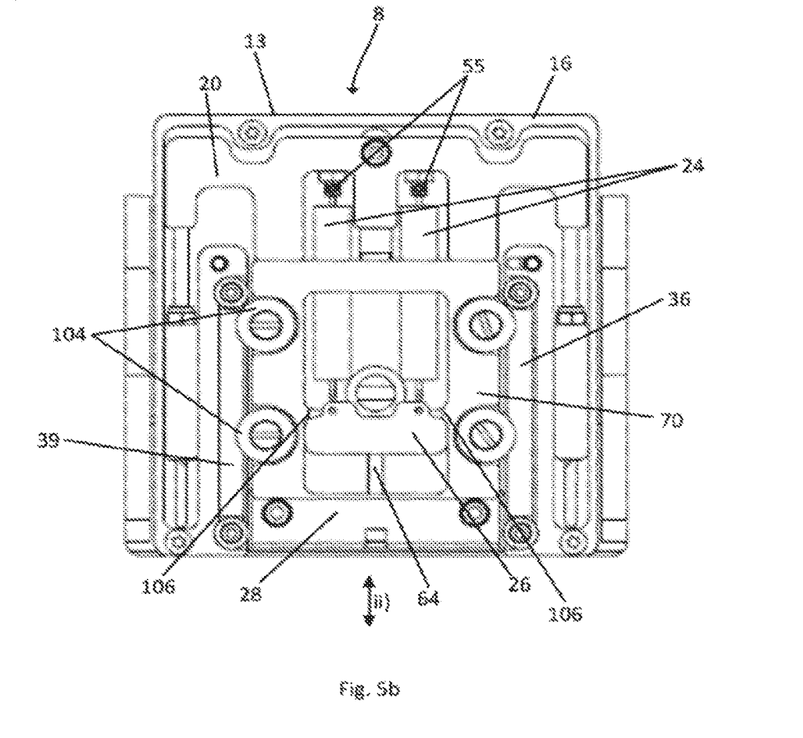

Referring to FIGS. 5a and 5b the functioning of the opening and closing mechanism 8 of the peristaltic pump 1 is now explained. FIGS. 5a and 5b, whereby FIG. 5a is a perspective view and FIG. 5b is a top down view of the same part of the peristaltic pump 1, illustrate the peristaltic pump 1 with the motor 2 and base plate 14 removed in order to make various parts of the opening and closing mechanism visible.

FIGS. 5a and 5b illustrate very well how the slider 20 is connected to the tube pressuring portion 28 via the elastic elements 24 and a bridge 26. The bridge 26 is connected to the tube pressuring portion 28 via an adjustment element 64 that is engaged in the tube pressuring portion 28 and a frame 70 of the tube pressuring portion 28, respectively, and the bridge 26. The elastic elements 24 are connected to the slider 20 via screws that for example comprise a hook, which can engage in a hook of the corresponding elastic element 24. The bridge 26 may comprise connecting protrusions 62 (FIG. 5a) comprising two holes for engaging hooks of the corresponding elastic elements 24. Thus the elastic elements 24 can be exchanged so that the elastic elements 24 or springs with different spring constants can be installed in the peristaltic pump 1. The connecting protrusions 62 are optional and not needed in order to achieve the function of the opening and closing mechanism 8.

The adjustment element 64 is shown as a single adjustment element 64. This is advantageous because only one adjustment element 64 is used to change the pre-tension, which is smooth and saves time. The adjustment element 64 allows the peristaltic pump to adjust various system pressures so that it will function optimally.

The frame 70 of the tube pressurizing portion 28 comprises four symmetrically arranged guiding elements 104 in the form of rollers. The frame 70 is fixedly connected to the tube pressuring portion 28 and forms part of it, the connection may be achieved via screw and thread combination. The frame 70 has a rectangular shape as seen in a top down view (FIG. 5b) the rectangular shape defining a cut-out 105 having a side walls 109, a bottom wall 107 and a top wall 111. For illustrative purposes the bottom wall 107, the stop wall 111 and the side walls 109 are only referenced in FIG. 5a. The side walls 109 each comprise a stop protrusion 106. The stop protrusions 106 have the function of stopping the movement of the bridge 26 towards the slider 20 when the adjustment element 64 in the form of a screw is rotated in order to adjust the pre-tension in the elastic elements 24. The bridge 26 can thus not move all the way to the top wall 111 and it is always possible to engage the adjustment element 64 again in the bridge 26, even when the adjustment element 64 is by mistake disengaged and the elastic elements 24 is drawn towards the slider 20 by the elastic elements 24. The adjustment element 64 may be engaged in the bottom wall 107 of the frame 70 and a bottom of the tube pressurizing portion 28 or in one of the two elements. In the illustrated embodiment the adjustment element 64 is embedded in the bottom wall of the tube pressurizing portion 28 and the bottom wall 107. As mentioned previously the elastic elements 24 are embodied in the form of springs. The top wall 111 comprises openings 108 (FIG. 5a) in order to let the elastic elements 24 pass through.

The guiding elements 104 are provided in the form of rollers connected to the side walls 107 of the frame 70, for example via screw-bearing combination. Although the four guiding elements 104 are illustrated in the embodiment shown, it is actually possible to provide only two or more than four guiding elements 104. The advantage with four guiding elements 104 is that the movement of the frame 70 and therewith the tube pressuring portion 28 is kinematically overdetermined and gap-free. Due to the first adjustable motion link 36 the system can be deformed until all four guiding elements 104 engage the first and second motion link 36, 39, respectively, which provides for a good angle stiffness of the movement. Referring now to FIG. 5b in can be seen that half of the guide elements 104 on one side wall 109 engage a first adjustable motion link 36 and the other half of the guide elements 104 on the other side wall 109 engage a second motion link 39. The first adjustable motion link 36 and the second motion link 39 form part of the back portion 16 of the housing 6 and are connected to the back portion 16 via screws. The first adjustable motion link 36 is adjustable via two screws that are screwed into a protrusion of the back portion 16, whereby said protrusion extends towards the top 13 of the peristaltic pump 1. A similar protrusion may be provided to connect the second motion link 39 to the back portion 16. The adjustability of the first adjustable motion link 36 is provided in order to make sure that the first adjustable motion link 36 and the second motion link 39 are as parallel as possible so that during movement as little friction as possible exists and that other forms of movement problems that can occur due to lacking accuracy can be avoided and minimized in order to provide a very smooth and precise movement. During the opening and closing of the pivotable cover 22 the tube pressurizing portion 28 and the slider 20 move in a direction indicated by arrow ii) in FIG. 5b. The first adjustable motion link 36 is thus adjustable in a direction at least more or less perpendicular to the direction indicated by the arrow ii).

In an embodiment that is not shown in the figures, only one adjustable motion link may be provided. The adjustable motion link may be engaged by the two guiding elements, one on each side, or, if more than two guiding elements, for instance four guiding elements are provided, by two guiding elements on each side.

FIG. 5b further illustrates that the elastic elements 24 are connected to the slider 20 by adjustable adapters 55 configured to hold the elastic elements 24. The adapters may be screwed into the slider 20 or connected to it via a thread-shaft and nut combination while the thread shaft comprises a hole in order to hold an end of each of the elastic elements 24. The adjustable adapters 55 allow to move the range of pre-tension, for example in Newton, of the opening and closing mechanism 8 and the force with which the tube pressurizing portion is pressed towards the rotor 4, respectively. This further increases application fields of the peristaltic pump 1 and it also provides a high flexibility.

In the in FIGS. 5a and 5b illustrated closed position of the pivotable cover 22 the frame 70 and the tube pressuring portion 28 are moved upwards towards the top 13 of the housing 6 and the back portion 16, respectively. Thus when the pivotable cover 22 is opened, the frame 70 and the tube pressuring portion 28 will move downwards away from the top 13 of the housing 6 and the separating wall 34 of the back portion 16, respectively, so that a tube can be positioned between the tube pressurizing portion 28 and the rotor 4 (not shown in FIGS. 5a and 5b). In order to further improve the movement of the tube pressurizing portion 28 and the frame 70 there may be gliding surfaces 68 (FIG. 5a) employed on the back portion 16 and the corresponding surfaces of the tube pressurizing portion 28. The gliding surfaces 68 may comprises an element polymer or similar material such as for example Teflon or the like. In particular a gliding surface 68 may be arranged between the separating wall 34 of the back portion 16 and the tube pressurizing portion 28 as indicated in FIG. 5a. Such gliding surfaces 68 increases the robustness of the opening and closing mechanism 8, it reduces friction and further provides a force absorption when the tube pressuring portion 28 is closed. These effects lead to an increased lifetime of the peristaltic pump and to an improved stiffness.

Still referring to FIG. 5a the tube receiving opening 100 on the pump outlet side 46 is illustrated. The tube receiving opening 100 has at least a partial V-shape 120 (or U-shape) that is configured to interact, as shown in FIG. 4, with the V-shape 116 of the tube engaging protrusion 92 of the outlet tube holder portion 32 in order to decrease and increase the tube receiving opening 100 on the pump outlet side 46 upon closing and opening of the pivotable cover 22. Similarly does the tube receiving opening 98 comprise a V-shape 112 (or U-shape) as illustrated in FIG. 1 that interacts with the V-shape 112 of the tube engaging protrusion 80 of the inlet tube holder portion 30 as shown in FIG. 4.

Figure 6:
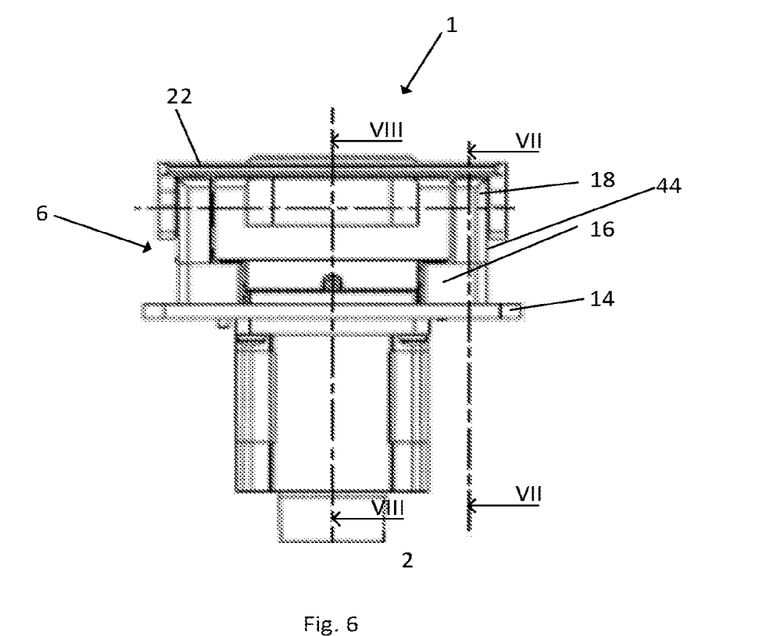
FIG. 6 schematically illustrates a bottom up view of the peristaltic pump according to the invention.

The functioning of the inlet tube holder portion 30 and the outlet tube holder portion 32 will now be explained referring to FIGS. 6 and 7. FIG. 6 is a bottom up view of the peristaltic pump 1 illustrating various elements previously explained, including the housing 6, the motor 2 and the base plate 14, the back portion 16 and the front portion 18 of the housing 6 and the pivotable cover 22.

Figure 7:
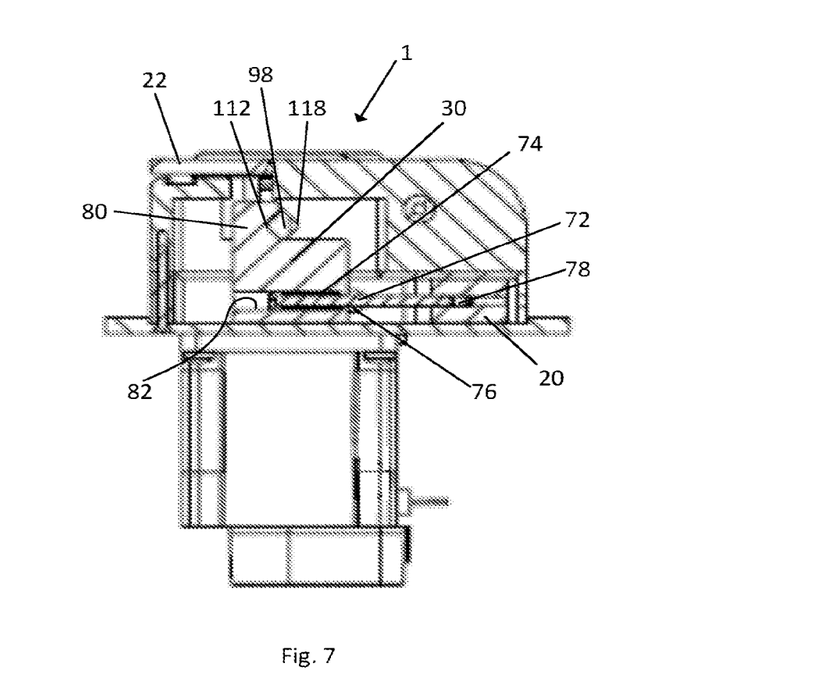
FIG. 7 illustrates a cross sectional view of the peristaltic pump according to the invention, the cross section being taken along line VII-VII of FIG. 6.

FIG. 7 is a cross sectional view of FIG. 6 through line VII-VII, thus through the inlet tube holder portion 30. The inlet tube holder portion 30 comprises a positioning element 72 in the form of a screw, which positioning element 72 is embedded in a recess 82 via an elastic element 74, here shown in the form of a spring. The positioning element 72 extends via a hole in the outlet tube holder portion 30 into the slider 20 so that the outlet tube holder 30 moves together with the slider 20 upon opening and closing of the pivotable cover 22. The position of the elastic element 74 can be adjusted and by rotating the positioning element/screw 72. This may be done in order to adjust the position and an initial pressure with which the V-shapes 112, 118 of the tube receiving opening 98 (FIG. 6) and the tube engaging portion 80, respectively, clamp or squeeze a tube when the pivotable cover 22 is in its closed position. In order to lock the position of the positioning element 72 the tube inlet holder portion 30 further comprises a stop element 78, illustrated in the form of a setscrew that fits and engages a thread in the slider 20, in which thread also the positioning element 72 is embedded but from an opposite side. The inlet tube holder portion 30 may further comprise a pre-tension device 76 for example in the form of a nut, which pre-tension device 76 is used to further adjust the pre-tension in the elastic element 74 once the position of the tube engaging protrusion 80 is set via the positioning element 72. The pre-tension element 76 is used to move the position of the tube engaging protrusion 80 in relation to the elastic element 74. The elastic element 74 is thereby arranged in between the tube engaging protrusion 80 and a head of the positioning element 72 so that a pre-tension can be achieved by changing the position of the pre-tension device 76.

The outlet tube holder portion 32 (illustrated in FIG. 4) may be similarly constructed and engaged in the slider 20 as the inlet tube holder portion 30 via an adjustment element and an elastic element. It may however be connected in a more simple way, for example via an elastic element that replaces the adjustment element and connects the slider to the outlet tube holder portion 32 so that it also moves together with the slider 20, as explained, upon closing and opening of the pivotable cover 22. It may be simpler constructed since the holding and temporary fixation of the outlet part of the tube is not that important and mainly fulfils a positioning and holding function, while the clamping and fixation of the tube in the tube receiving opening on the pump inlet side is of more interest since a slippage of the tube on the pump inlet side 44 should be avoided. The tube may however be fixed outside of the peristaltic pump 1 and thus the inlet- and outlet tube holder portion may not be present at all in the peristaltic pump 1.

Figure 8:
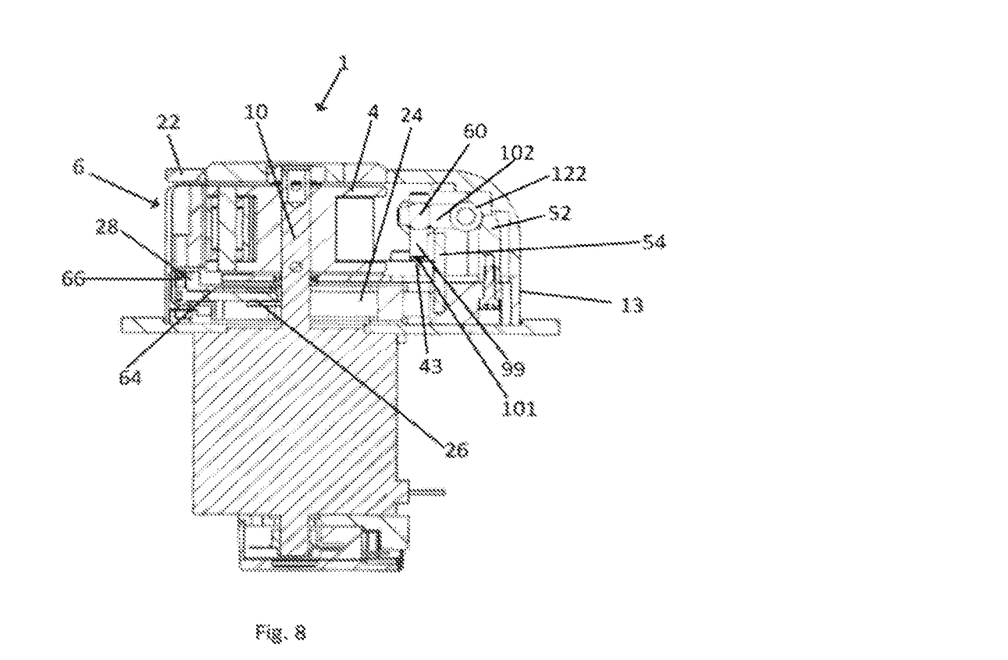
FIG. 8 illustrates a cross sectional view of the peristaltic pump according to the invention, the cross section being taken along line VIII-VIII of FIG. 6.

Turning now to FIG. 8, which FIG. 8 is a cross sectional view of FIG. 6 through line VIII-VIII, thus through the center of the peristaltic pump 1. FIG. 8 further illustrates how the adjustment element 64 of the tube pressurizing portion 28 engages the bridge 26. Once the pre-tension in the elastic elements 24 is set, the adjustment element 64 can be locked via a stop element 66, illustrated in the form of a setscrew/screw.

The pivotable cover 22 is shown in its closed position and it is well visible, how the post 52 of the slider 20 engages the roller 122 mounted at the first extension 102 of the rotating shaft 60 of the pivotable cover 22. When the pivotable cover 22 is closed the roller 122 is in contact with the chamfered free end of the post 52 in order to provide an initial resistance to the pivotable cover 22 prior to opening and also to provide a soft "snap" feeling upon closing of the pivotable cover 22, due the force in the tension elements 24 and the shape of the free end of the post 52. As can well be seen from FIG. 8, the pin 54 is engaged by the roller 122 once the pivotable cover 22 is opened more than a certain, predetermined angle. This angle may be chosen to be in a suitable range. As soon as the pivotable cover 22 is moved above or beyond this angle the roller 122 is starting to engage the pin 54 and pushes the slider 20 away from the top 13 and therewith lets the tube pressurizing portion 28 and the tube inlet holder portion 30 (not shown in FIG. 8) and the tube outlet holder portion 32 (also not shown in FIG. 8) move or glide away from the top 13 of the peristaltic pump 1 and the rotor 4, respectively. The post 52 may be fixedly connected to the slider 20 via a screw/thread connection. It is to be noted that when the pivotable cover 22 is opened then the slider 20 and the frame 70 and tube pressurizing portion 28, respectively, do not move together from the beginning of the movement rather only after the pivotable cover 22 is opened beyond said suitable angle.

FIG. 8 further also illustrates well how the drive axis 10 extends through the housing 6 and engages the rotor 4. Further the second extension 99 comprising the sensor element 101 that is configured to engage and interact with the sensor 43 is also visible in FIG. 8.

Figure 9:
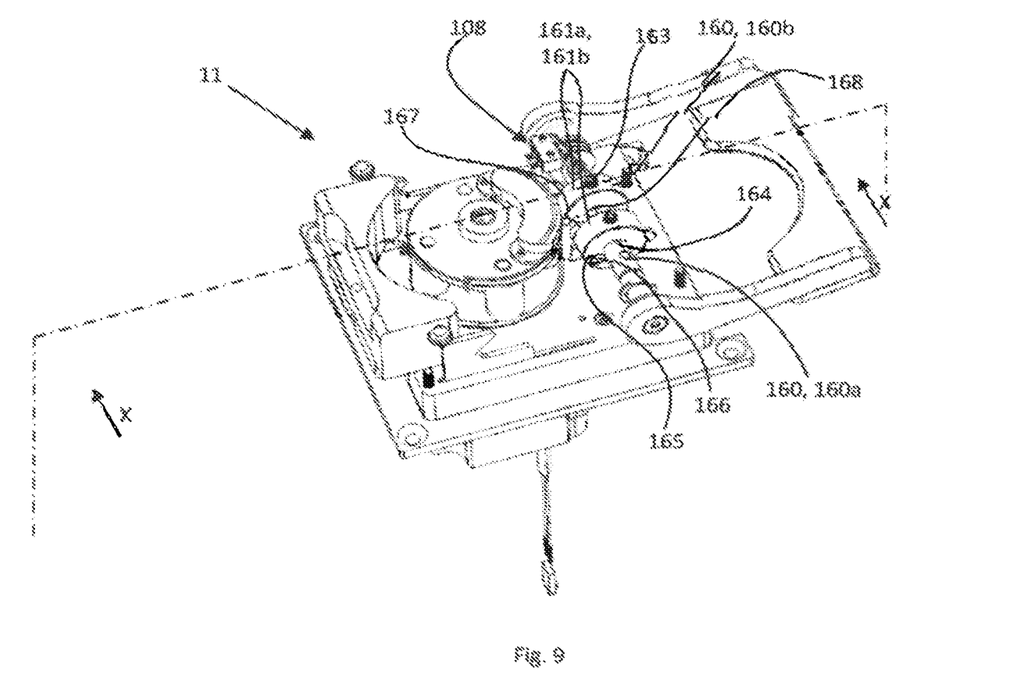
FIG. 9 schematically illustrates a perspective view of another embodiment of the peristaltic pump according to the invention, with a housing removed.

FIG. 9 illustrates a perspective view of a different embodiment of the peristaltic pump 11, whereby the housing is removed for illustrative purposes. The difference concerns the opening and closing mechanism 108 and the rotating shaft 160. Note that only the parts that differ from the previous embodiment shown in FIGS. 1 to 8 will be described. The slider 20 remains unchanged for instance. Some elements that are connected to the slider 20 however differ from the embodiment shown previously, such as the pin 54 and the post 52. The shaft 160 is divided in two shaft parts 160*a*, 160*b*, each of the parts 160*a*, 160*b* is embedded with one end in the housing (not shown) and with another end in a disc-shaped piece 161*a*, 161*b*, which disc-shaped pieces 161*a*, 161*b* each have a diameter greater than the shaft parts 160*a*, 160*b*. The shaft parts 160*a*, 160*b* are further connected to the pivotable cover 22 via one end. The disc-shaped pieces 161*a*, 161*b*, each comprise a hole 164 for receiving the corresponding shaft part end and the disc-shaped pieces 161*a*, 161*b* further each comprise a set screw 163 for clamping the respective disc shaped piece 161*a*, 161*b* to the corresponding shaft part 160*a*, 160*b* and shaft part end, respectively.

The disc-shaped pieces 161*a*, 161*b*, each comprise a recess 165. The recess 165 is located eccentric on the disc shaped pieces 161*a*, 161*b* and also eccentric versus the shaft parts 160*a*, 160*b*, so that an eccentric shaft 166 or the like can be arranged within the recess 165 so that the eccentric shaft 166 extends between the two disc-shaped pieces 161*a*, 161*b*. The eccentric shaft 166 may comprise a ball-bearing 167, as illustrated in FIG. 9 or another ring-shaped element (not shown) that can be rotated when the disc-shaped pieces 161*a*, 161*b* are rotated, for example upon opening or closing the pivotable cover 22. The disc-shaped pieces, 161*a*, 161*b*, the eccentric shaft 166 and the ball bearing 167 may together form the first extension 102 (c.f. FIG. 8), as previously explained.

The shaft parts 160*a*, 160*b* may be partially flattened at their end engaging the disc-shaped pieces 161*a*, 161*b* so that the set screw 163 can engage a flattened surface 168 for better engagement.

Figure 10:
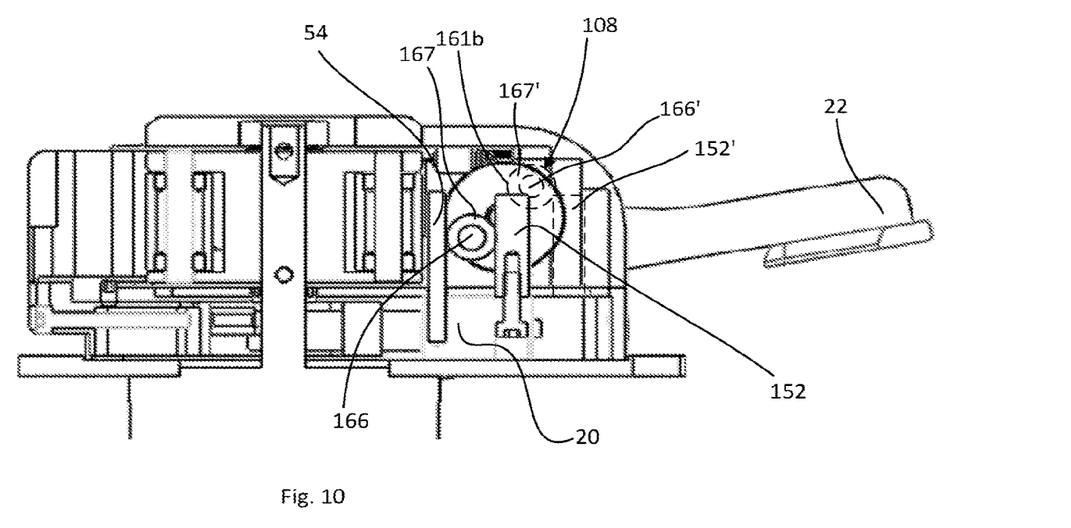
FIG. 10 illustrates a view onto a cross section of the embodiment according to FIG. 9 cut along plane X-X.

Turning now to FIG. 10, the opening and closing mechanism 108 illustrated in FIG. 9, is further explained. The slider 20 still comprises the pin 54 as previously described and with the same function but the post 152 is designed in a different manner and does not comprise a chamfered free end any longer but rather a cylindrical shaped free end.

FIG. 10 further illustrates how the position of the eccentric shaft 166', the ball bearing 167' and the post 152' change when the pivotable cover 22 is in the closed position (not shown). The positions of the eccentric shaft 166', the ball bearing 167' and the post 152' are indicated with dashed lines. It can be seen that the centre of the shaft 166' and the ball bearing 167' is positioned above a top surface of the post 152' when the pivotable cover 22 is in the closed position (not shown). This creates a force in a closing direction of the pivotable cover 22 and an operator will feel when the pivotable cover "clicks" in its closed position. The same will happen when the pivotable cover 22 is opened, the positioning of the centre of the shaft 166' and the ball bearing 167' versus the top surface of the post 152' creates a "click" that can be felt by an operator. The "click" is generated when the ball bearing 167' is transferring from the edge of the post 152' to the side surface of the post 152'. The described positioning of the eccentric shaft 166', the ball bearing 167' and the top surface of the post 152' leads to the outcome that an upper edge of the post 152, 152' is pushing the ball bearing 167' towards a closed position of the pivotable cover 22 and the housing 6, respectively, when the pivotable cover 22 is in the closed position (not shown in FIG. 10).

The interaction between the pin 54 and the eccentric shaft 166, 166' and the ball bearing 167, 167' is the same as previously described and concerns the movement of the slider 20 via the pin 54, when the pivotable cover 22 is moved from the closed position to the open position via the disc-shaped pieces 161a, 161b, the ball bearing 167 and the eccentric shaft 166, respectively.

Figure 11:
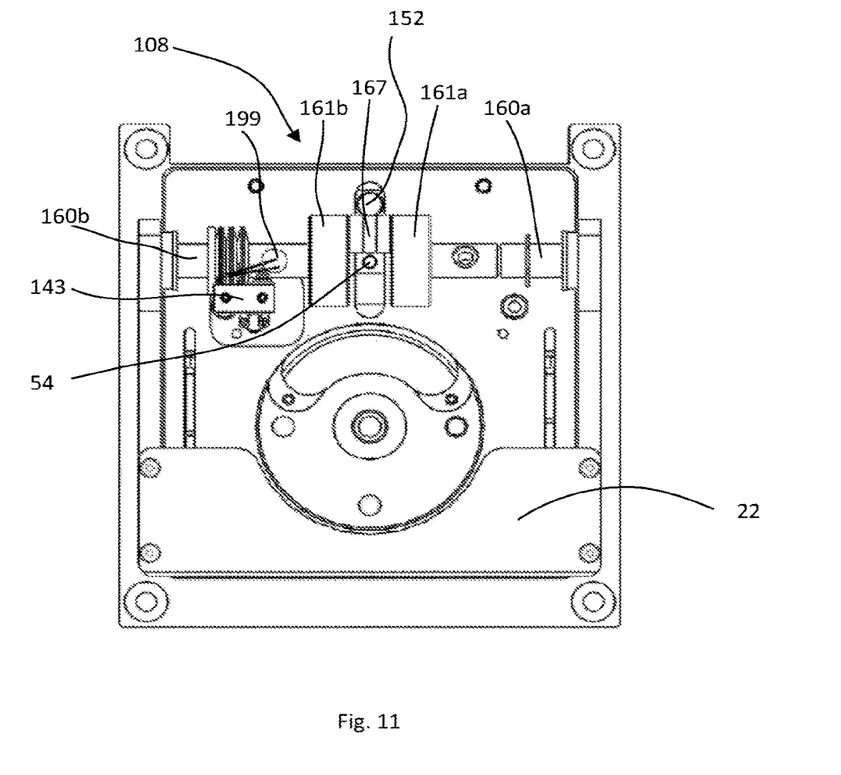
FIG. 11 illustrates a top down view onto the embodiment of FIG. 9 with the pivotable cover closed and the housing removed.

FIG. 11 illustrates a top down view on the opening and closing mechanism 108 described in connection with FIGS. 9 and 10. In FIG. 11 the disc-shaped pieces 161a, 161b, the shaft parts 160a, 160b, the ball bearing 167, the post 152 and the pin 54 are well illustrated. The pivotable cover 22 is in its closed position. From FIG. 11 it is further visible that the second extension 199 interacting with the sensor 143 is positioned slightly different as in the embodiments shown in FIGS. 1 to 8. The second extension 199 is connected to the shaft 160 and the shaft part 160b, respectively, so that it can make contact with the sensor 143, which sensor 143 is now positioned above the shaft 160 close to the housing 6 (c.f. FIG. 3), when the pivotable cover 22 reaches the closed position. The sensor 143 is mounted on an inside of the front portion 18, such as the roof portion of the front portion 18, and press fitted to it using one, two or more pins or the like and/or an adhesive.

As indicated above, the first extension 102 comprising a roller 122 explained referring to FIG. 8, can be seen as the shaft 166 and the two disc-shaped pieces 161a, 161b. The roller 122 may be seen as the ball bearing 167. Thus the term first extension 102 also covers the solution of the opening and closing mechanism 108 shown in FIGS. 9 to 11.

As mentioned herein the elastic elements 24, 74 may be springs, rubber elements or other kind of dampers that are elastic. Further also the various adjustment elements 64, 72 may be screws, or other types of adjustable elements such as gear racks or the like.

The invention has now been described referring to a specific embodiment. The skilled person may however conceive that certain elements or mechanisms of the peristaltic pump may be designed differently. Such different designs are considered to fall within the scope of the present invention.

What is claimed is:

1. A peristaltic pump comprising:
a motor;
a rotor coupled to the motor;
a housing in which the rotor is arranged, the housing extending from a bottom to a top; and
an opening and closing mechanism including a tube pressuring portion, a slider, and a pivotable cover coupled to the housing and the slider, the slider being connected to the tube pressuring portion such that a tube engaging surface of the tube pressuring portion slides towards and away from the rotor upon closing and opening of the pivotable cover, which opens and closes by pivoting around a central axis of a rotating shaft, respectively, wherein the central axis of the rotating shaft is located proximate to the bottom of the housing and the tube pressuring portion is located proximate to the top of the housing;
wherein the housing includes a first motion link, the tube pressuring portion includes a frame that extends into the housing, the frame having at least one guiding element,
wherein movement of the tube pressuring portion towards and away from the rotor is guided by the at least one guiding element, which interact with the first motion link, and
wherein the tube pressuring portion includes an adjustment element configured to move the tube engaging surface of the tube pressuring portion toward and away from the rotor to adjust the peristaltic pump to various system pressures, the opening and closing mechanism further including a slider moving element attached to the slider, the rotating shaft of the pivotable cover having an extension configured to engage the slider moving element for moving the slider and also the tube pressuring portion away and towards the top of the housing in response to a respective opening and closing of the pivotable cover.

2. The peristaltic pump according to claim 1, wherein the opening and closing mechanism further includes an elastic element connected to the slider and the tube pressuring portion, wherein the elastic element is connected to the adjustment element such that tension in the elastic element is adjustable.

3. The peristaltic pump according to claim 2, wherein via the elastic element the tube pressuring portion is moved away and towards the top of the housing in response to the respective opening and closing of the pivotable cover.

4. The peristaltic pump according to claim 2, including a bridge connecting the adjustment element to the elastic element, wherein the frame comprises a cut-out having a bottom wall and two side walls that each have a stop protrusion, and wherein the bridge is movably arranged in the cut-out between the bottom wall and the stop protrusions.

5. The peristaltic pump according to claim 4, wherein the elastic element includes two elastic elements connected to the adjustment element via the bridge, and wherein the two elastic elements are symmetrically and parallel-connected to the bridge.

6. The peristaltic pump according to claim 2, wherein:
the housing includes a front portion and a back portion;
the rotor is arranged in the front portion; and
the slider, the elastic element, the frame, the adjustment element, and the first motion link are arranged in the back portion.

7. The peristaltic pump according to claim 2, wherein the tube pressuring portion includes a stop element configured to engage the adjustment element such that the adjustment element cannot move any longer once tension in the elastic element is set.

8. The peristaltic pump according to claim 2, further including an adjustable adapter, wherein the elastic element is connected to the slider via the adjustable adapter.

9. The peristaltic pump according to claim 2, wherein the elastic element is a spring and wherein the adjustment element is a screw.

10. The peristaltic pump according to claim 1, wherein the slider moving element is a post.

11. The peristaltic pump according to claim 10, wherein:
the slider includes a pin extending in a same direction from the slider as the post, the pin arranged in line with the post as seen in a direction perpendicular to a longitudinal direction defined by the rotating shaft,
the extension includes a roller that engages the post upon closing of the pivotable cover for moving the slider towards the top of the housing, and the roller engages the pin upon opening of the pivotable cover for moving the slider away from the top of the housing.

12. The peristaltic pump according to claim 1, wherein the extension extends perpendicular to a longitudinal direction defined by the rotating shaft.

13. The peristaltic pump according to claim 1, further including a second motion link, wherein the frame includes four guiding elements, whereby two of the four guiding elements engage the first motion link and other two of the four guiding elements engage the second motion link.

14. The peristaltic pump according to claim 13, wherein at least two of the four guiding elements are rollers with a U- or V-shaped profile and wherein the first motion link and the second motion link are bars configured to fit into the U- or V-shaped profile of the rollers.

15. The peristaltic pump according to claim 1, wherein:
the housing includes a pump inlet side and a pump outlet side, each of the pump inlet side and the pump outlet side having a tube receiving opening, and
the opening and closing mechanism further includes an inlet tube holder portion and an outlet tube holder portion, the inlet tube holder portion and the outlet tube holder portion arranged next to the pump inlet side and the pump outlet side, respectively, and the inlet tube holder portion and the outlet tube holder portion being configured to increase and decrease a size of its corresponding tube receiving opening upon opening and closing of the pivotable cover.

16. The peristaltic pump according to claim 15, wherein:
an elastic element connecting the inlet tube holder portion to the slider is connected to the inlet tube holder portion via a positioning element in order to adjust a position of the inlet tube holder portion; and
the inlet tube holder portion further includes a pre-tension device configured to be screwed onto the positioning element in order to provide a pre-tension in the elastic element connecting the inlet tube holder portion to the slider.

17. The peristaltic pump according to claim 16, wherein the inlet tube holder portion includes a stop element configured to engage the positioning element in order to lock the positioning element after a tension in the elastic element connecting the inlet tube holder portion to the slider has been set.

18. The peristaltic pump according to claim 1, wherein the rotating shaft includes a sensor element, the housing includes a sensor, and the sensor element and the sensor are arranged to detect whether the pivotable cover is open or closed.

19. The peristaltic pump according to claim 1, wherein the rotating shaft is divided into two shaft parts, and the opening and closing mechanism further comprises:
an eccentric shaft; and
two disc-shaped pieces each having a centrally positioned hole and an eccentrically positioned recess, whereby the two shaft parts are embedded with one end in the housing and with another end in the corresponding centrally positioned hole in the respective two disc-shaped pieces and whereby the eccentric shaft extends from the eccentrically positioned recess in one of the two disc-shaped pieces to the eccentrically positioned recess of an other one of the two disc-shaped pieces such that the eccentric shaft interconnects the two disc-shaped pieces in an eccentric manner.

20. The peristaltic pump according to claim 19, wherein the opening and closing mechanism further includes a ball bearing configured to be arranged around the eccentric shaft, the ball bearing configured to engage the slider moving element.

* * * * *